United States Patent [19]

Scholar et al.

[11] Patent Number: 5,552,390
[45] Date of Patent: Sep. 3, 1996

[54] PHOSPHOROTHIOATE INHIBITORS OF METASTATIC BREAST CANCER

[75] Inventors: Eric M. Scholar; Patrick L. Iversen, both of Omaha, Nebr.

[73] Assignee: The Board of Regents of The University of Nebraska, Lincoln, Nebr.

[21] Appl. No.: 164,200

[22] Filed: Dec. 9, 1993

[51] Int. Cl.$^6$ ............... A61K 48/00; C07H 21/04
[52] U.S. Cl. ............... 514/44; 536/23.1; 536/24.5; 435/240.2; 935/34
[58] Field of Search ............... 514/44; 536/23.1, 536/24.5; 435/6, 240.2; 935/34

[56] References Cited

PUBLICATIONS

Stull et al (1995) Pharmaceutical Research 12:465–483.
Wu Pong (1994) Pharmaceutical Technology 18:102–114.
Miller et al (1994) Parasitology Today 10: 92–97.
Wagner (1994) Nature 372:333–335.
C. A. Stein et al (1993) Science 261:1004–1012.
R. Weiss (1991) Science News 139:108–109.
P. Westermann et al (1989) Biomed Biochim Acta 48:85–93.
J. F. Milligan et al (1993) J Med. Chem. 36:1923–1937.
M. J. Grusby et al. (1990) Nucleic Acids Research 18:4008.
P. Verde et al (1984) Proc Natl Acad Sci, USA, 81:4727–4731.
A. Riccio (1985) Nucleic Acids Research 13: 2759–2771.
P. Rørth (1990) Nucleic Acids Research 18: 5009–5017.
R. K. DeLong et al (1991) J Cell. Biochem. Suppl. Ø (15 part D) p. 30.
J–Y Zhang et al. (1992) Cancer Research 52:6682–6689.
R. Reich et al (1988) Cancer Research 48:3307–3312.
P. Huhtala et al (1991) J Biol Chem 266:16485–16490.
Cole, S. P., 1986, Rapid Chemosensitivity Testing Of Human Lung Tumor Cells Using The MTT Assay, Cancer Chemother. Pharmacol. 17:259–263.
Dano, K. et al, 1985, Plasminigen Activators To Sugar Degradation In Cancer, Adv. Cancer Res., 44:139–266.
Hagiya et al, 1992, Urokinase–Type Plasminogen Activator And Its Specific Receptor In High Metastatic And Non Metastatic Cell Lines Derived From Human Lung Adenocarcinoma, Thromb. Res. 65(3):449–56.
Heron Yu, Dec. 1990, Relationship Between Secreted Uronkinase Plasminogen Activator Activity And Metastatic Potential In Murine B16 Cells Transfected With Numan Urokinase Sense And Antisense Genes, Cancer Research 50:7623–7633.
Liotta, L. A., 1991, Cancer Metastasis And Angiogenesis: An Imbalance Of Positive And Negative Regulation, Cell 64:327–336.
Loke, S. L., 1989, Characterization Of Oligonucleotide Transport Into Living Cells, Proc. Nat'l. Acad. Sci USA 876;3474–3478.
Miller et al., 1983, Characterization Of Metastatic Heterogeneity Among Subpopulations Of A Single Mouse Mammary Tumer: Heterogeneity In Phenotypic Stability Invasion And Metastasis. Invasion Metastasis, 3:22–31.
Pereyra–Alfonso, S., 1988, Correlation Of Urokinase Type Plasmin Activator Production And Metastacity Of Two Murine Mammary Adeno Carcinoma, Int. J. Cancer 42:59–63.
Reiter et al., 1993, The Role Of Urokinase Receptor In Extracellular Matrix Degradation By HT29 Human Colon Carcinoma Cells, Int. J. Cancer 53(3):444–450.

(List continued on next page.)

*Primary Examiner*—Bruce R. Campbell
*Attorney, Agent, or Firm*—Zarley, McKee, Thomte, Voorhees, & Sease

[57] ABSTRACT

A method of inhibiting tumor invasion and metastasis of cancer cells using antisense oligonucleotides is disclosed. Phosphorothioate oligos were developed which are complementary to proteolytic enzymes such as urokinase plasminogen activator which are associated with invasion. In vitro and in vivo experiments with these oligos demonstrated highly significant reduction in tumor invasion and metastasis of mammary carcinoma cells.

25 Claims, 2 Drawing Sheets

ANTI-SENSE OLIGONUCLEOTIDES FOR INHIBITION OF BREAST CANCER METASTASIS

OTHER PUBLICATIONS

Sugimura–M et al, 1992, Clinical Significance Of Urokinase–Type Plasminogen Activator In Invasive Cervical Cancer Of the Uterus, Gynecol–Oncol 46(3):330–336.

Vindeløv, L., 1983, Standardization Of High–Resolution Flow Cytometric DNA Analysis By The Simultaneous Use Of Chicken And Trout Red Blood Cells As Internal Reference Standards. Cytometry, 3:328–331.

Yagel, S., 1989 Mechanism Of Cellular Invasiveness: A Comparison Of Amnion Invasion In Vitro And Metastatic Behavior In Vivo. J. Natl. Cancer. Inst., 81:768–775.

PHOSPHOROTHIOATE INHIBITORS OF METASTATIC BREAST CANCER

BACKGROUND OF THE INVENTION

Cancers, of which there are an estimated 200 different kinds, have the common property of uncontrolled growth of cells derived from normal tissues. More than 900,000 new cases of cancer are diagnosed annually in the United States and there are 600,000 deaths from cancer each year.

Despite considerable success in the treatment of several specific tumors, the overall survival rate for most cancers has not changed dramatically over the past few years. Surgery and combination chemotherapy have proved successful in the treatment of early localized disease but the development of clinical metastases, or spread of cancer to distal sites, remains the primary cause of cancer morbidity and mortality. Metastatic disease is incurable with a median survival of 2.2 years from the time of documented metastasis.

Metastasis describes the movement of cancer cells from one part of the body to the other causing spread of cancer to areas of the body apart from the primary growth. Metastasis is a dynamic process that involves a sequence of interrelated steps involving tumor cell adhesion to, and subsequent digestion, of basement membranes, intravasation into and survival in the vasculature, extravasation out of the vasculature at distant sites followed by growth in a distant organ environment.

Tumor invasion through tissue barriers and into lymph and blood vessels involves both mechanical and enzymatic processes. Tumors are known to contain and secrete various proteolytic enzymes such as urokinase plasminogen activator, metalloproteinases cathepsin-B, gelatinase, heparinase, and collagenase. Many malignant neoplasms produce higher levels of these proteolytic enzymes than benign tumors or corresponding normal tissues.

These enzymes have been shown to be active in most types of metastatic cancer including breast cancer; colon cancer, Reiter et al., The Role of Urokinase Receptor in Extracellular Matrix Degradation by HT29 Human Colon Carcinoma Cells, int. J. Cancer 53(3):444–50 (1993); epidermal carcinoma, Testa, "Loss of the Metastatic Phenotype by a Human Epidermoid Cell Line HEp-3 is Accompanied by Increased Expression of Tissue Inhibitor of Metalloproteinase 2, Cancer Res. 52(20):5597–603 (1992); lung adenocarcinoma, Hagiya et al, Urokinase-Type Plasminogen Activator and Its Specific Receptor in High Metastatic and Non Metastatic Cell Lines Derived From Human Lung Adenocarcinoma, Thromb. Res. 65(3):449–56, 1992; and cervical cancer, Sagimura-M et al, Clinical Significance of Urokinase-Type Plasminogen Activator in Invasive Cervical Cancer of the Uterus, Gynecol-Oncol 46(3):330–336 (1992). Invasion also involves an initial adhesion to the basement membrane and after enzyme digestion motility of the invasive cells occurs. The ideal anti-invasion agent would be one that inhibited one or more of these steps without significant toxicity.

Several different approaches to inhibiting invasion have been tried with limited success. The use of inhibitors of degradative enzymes that are involved in the invasive process is one approach that has been used often with varying degrees of success. Liotta, L. A., Steeg, P. S. and Stetler-Stevenson, W. G. Cancer Metastasis and Angiogenesis: An Imbalance of Positive and Negative Regulation. Cell, 64:327–336, 1991. This invention comprises a new strategy for inhibiting tumor invasion by inhibiting production of the proteolytic enzymes essential for tumor invasion and metastasis by use of phosphorothioate oligonucleotides.

Breast cancer remains a particularly significant metastatic disease due to its high prevalence. American women have a one in nine risk of developing breast cancer in their lifetime. The initial step in the proper treatment for breast cancer is the excisional biopsy followed by a definitive surgical procedure.

Unfortunately it has been shown that randomized patients of radical mastectomy versus simple mastectomy plus minus nodal radiation showed that surgery did not increase survival. Axillary nodal dissection was effective as a staging procedure but did not prolong survival. Regardless of the surgical procedure; patients failed systematically, i.e. bone, liver, lung, skin, brain metastatic lesions were found. Therefore, the treatment approach for breast cancer has undergone a dramatic evolution toward breast conservation procedures. Medial resection is followed by either adjuvant chemotherapy or endocrine therapy to eradicate micrometastasis reflecting the current approach that all invasive cancers be viewed as potentially metastatic to optimize survival.

A number of prognostic indicators have been helpful in identifying patients at risk for relapse. They include axillary lymph node involvement with tumor, tumor size, histopathological classification, histologic grade and nuclear grade, estrogen receptor, progesterone receptor, DNA ploidy and S-phase fraction. The presence of axillary lymph node involvement with tumor remains the strongest predictor of recurrence and survival. The relapse rate at 10 years increases direction proportionally with the number of axillary lymph node involvement with tumor ranging from 20% for patients without lymph node involvement with term to 60% for 1 to 3 lymph node to 85% for greater than 4 lymph noes involved with tumor. Tumor size is the second most important prognostic indicator.

Breast cancer is clearly a heterogeneous tumor at presentation. Unfortunately, currently available detection methods and prognostic indicators have major limitations, being unable to detect micrometastatic disease, or cells capable of early metastasis, or identify clones of cells with drug resistance.

Clearly a need exists in the art to inhibit metastasis, as a follow up to surgery or an initial treatment at diagnosis.

It is an object of the present invention to provide a method of inhibiting metastasis of cancer cells by treatment with antisense oligonucleotides.

It is another object of the invention to provide antisense phosphorothioate oligonucleotides complementary to the mRNA of protease enzymes involved in tumor invasion to block translation of these proteins.

Yet another object of the present invention is to provide antisense oligonucleotides which are nuclease resistant and non toxic.

Yet another object is to provide antisense oligonucleotides to urokinase plasminogen activator which inhibit metastasis in highly metastatic breast cancer cells.

Other objects of the invention will become apparent from the detailed description of the invention which follows.

SUMMARY OF THE INVENTION

The present invention relates to a method of inhibiting tumor invasion and metastasis of cancer cells through activity of modified oligonucleotides. According to the present invention, a synthetic oligonucleotide of at least 6 nucleotides, which is complementary to DNA (antigene) or RNA (antisense), and which interferes with the process of transcription or translation of proteolytic enzymes essential for cancer cell invasion and metastasis is presented as a new therapy for treatment of cancer. The synthetic oligo blocks expression of protease enzymes essential for tumor invasion through the basement membrane and into the blood and lymphatic tissues.

Antisense oligonucleotides represent potential tools in research and therapy by virtue of their ability to specifically inhibit synthesis of target proteins. A major theoretical advantage of these oligos is their potential specificity for binding to one site (mRNA) in the cell. According to the invention the oligo is introduced to cells under conditions appropriate for hybridization of complementary nucleotide sequences. It is postulated that under such conditions, hybridization of proteolytic enzyme mRNA with the introduced complementary oligo occurs, effectively blocking translation. The nucleotide sequences of the modified oligos which inhibit synthesis of these enzymes need not be wholly (100%) complementary to be useful in the present invention. They are chains of nucleotides approximately 17–25 nucleotides that are capable of reducing synthesis of proteolytic enzymes.

Traditional limitations of antisense therapy have been preparation of the oligonucleotide analogue which is substantially resistant to the endo and exonucleases found in the blood and cells of the body. Several modifications to these oligos has helped alleviate this problem.

Modified or related nucleotides of the present invention can include one or more modifications of the nucleic acid bases, sugar moieties, internucleoside phosphate linkages, or combinations of modifications at these sites. The internucleoside phosphate linkages can be phosphorothioate, phosphoramidate; methylphosphonate, phosphorodithioate and combinations of such similar linkages (to produce mix backbone modified oligonucleotides). Modifications may be internal or at the end(s) of the oligonucleotide molecule and can include additions to the molecule of the internucleoside phosphate linkages, such as cholesteryl, diamine compounds with varying numbers of carbon residues between the amino groups, and terminal ribose, deoxyriboase and phosphate modifications which cleave, or crosslink to the opposite chains or to associated enzymes or other proteins which bind to the genome.

These modifications traditionally help shield the oligo from enzymatic degradation within the cell. The present invention discloses several phosphorothioate oligonucleotides which are antisense to urokinase-type plasminogen activator and other proteolytic enzymes which were found to drastically reduce tumor cell invasion and metastasis of breast cancer cells.

DETAILED DESCRIPTION OF THE INVENTION

Figure 1:
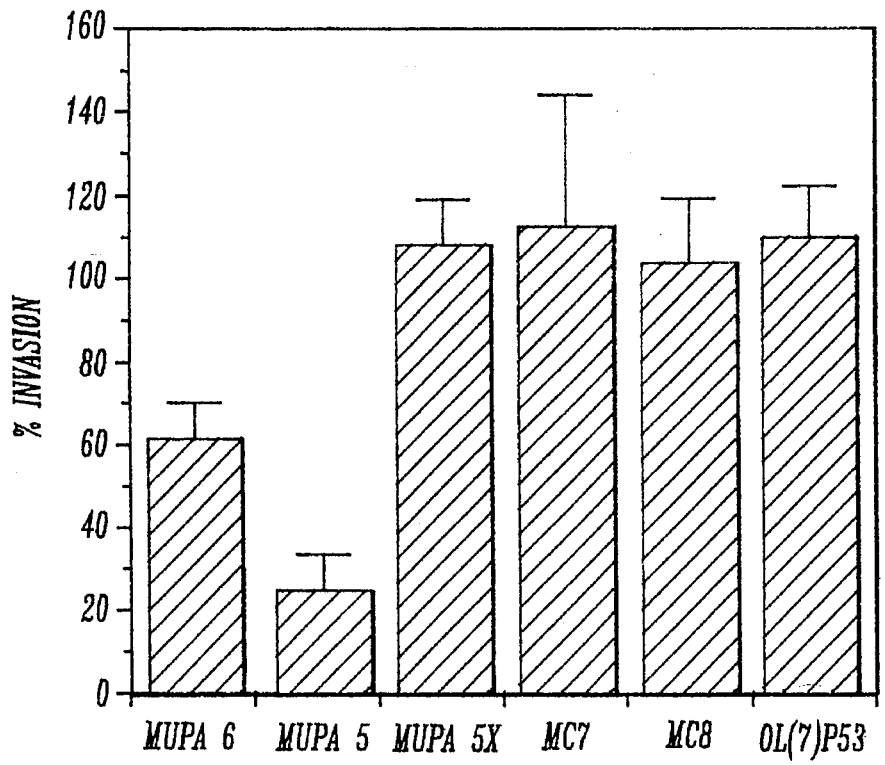
FIG. 1 is a graph depicting the present cell invasion for cells treated with the antisense oligos of the present invention.

The modified oligonucleotides of the present invention can be administered to an individual to provide a reduction in metastasis of breast cancer cells. Traditionally administration would be conducted immediately after detection of presence of breast cell cancer to maintain the oligonucleotides in the blood stream. They could also be used in combination with surgery to catch the window of migration and prevent further metastatic action via the blood. The oligonucleotides of the present invention also could be used at chronic (or stage IV) breast cancer to reduce metastatic spread any further.

The modified oligonucleotides are administered to an individual generally as a component of a composition which also includes a physiologically acceptable carrier. Modified oligonucleotides of the present invention could be administered to individuals in any manner capable of getting the oligonucleotides initially into the bloodstream and subsequently into the cells. Suitable administration procedures include intravenous injection, intravenous drip or oral form (e.g. in capsule or tablet form). The dose to be administered varies for such factors as the size and age of the patient, the state of the disease and type of modified oligonucleotide to be given.

While not wishing to be bound by any theory, it is postulated that after administration the oligonucleotides enter cells, hybridize to mRNA which is translated to produce the proteolytic enzymes essential for cancer cell invasion and inhibit its ability to serve as a template for synthesis of encoded products. Whatever the mechanism of action, as a result, proteolytic enzymes necessary for metastasis are not produced and correspondingly metastasis is inhibited.

In a preferred embodiment the oligonucleotide will have a phosphorothioate modification. A phosphorothioate oligonucleotide is a DNA analogue with a sulfur replacing one of the nonbridging oxygen atoms bound to the phosphate backbone which causes the oligonucleotide to be nuclease resistant.

Phosphorothioate oligonucleotides have been shown to be stable in serum, cell homogenates, intact cells and in the intact animal. Crooke R. M. (1991) In vitro Toxicology and Pharmacokinetics of Antisense Oligonucleotides. Anti-Cancer Drug design. 6:531–538. Further these oligonucleotides are transported into living cells LokeS. L., Stein, C. A., Zhang, X. H., Mori, K., Nakanisho, M., Subasinghe, C., Cohen, J. S. and Neckers, L. M. (1989) Characterization of Oligonucleotide Transport into Living Cells. Proc. Nat'l. Acad. Sci. U.S.A. 86:3474. The combined effects of oligonucleotide stability and transport into living cells provides mechanistically favorable opportunities for an improved class of metastatic inhibitors.

Another advantage of phosphorothioate oligonucleotides has been their low toxicity. Phosphorothioate oligonucleotides complementary to the rev mRNA of the human imunodeficiency virus (HIV), exon 10 of p53 mRNA (identified as OL(1)p53), and the initiation of translation region of c-myb mRNA phosphorothioate oligonucleotides have been administered to mouse, rat, and rhesus monkey for toxicity evaluation. All of these studies were employed using dose exposure escalating studies and no major toxicity was observed.

It is well known in the art that pharmacokinetic analysis of phosphorothioate oligonucleotides has demonstrated a range of half-lives, distribution and availability based on the nucleic acid composition of the oligonucleotide.

Thus, the potential to develop an antimetastatic agent with favorable pharmacokinetic parameters is highly likely. The elimination half-life should be long enough to provide a basis of convenient dose schedules and observed volumes of distribution indicate oligonucleotides are probably bioavailable in the body. Hence, cells with metastatic potential are likely to be exposed to the oligonucleotide while in transit in the body.

Thus in accordance with the present invention, phosphorothioate oligonucleotides are developed which are complementary to the mRNA of proteolytic enzymes to reduce synthesis and inhibit tumor cell invasion. These protease enzymes can include collagenases, cathepsin D, urokinase type plasminogen activator, or any other protease necessary for tumor cell invasion.

Urokinase is a protease that activates plasminogen to the enzyme plasmin. Plasminogen is ubiquitous in extracellular fluids and its active form (plasmin) has a general proteolytic activity that is believed to facilitate translocation of tumor cells through the extracellular matrix. Plasmin has been shown to have the ability to directly degrade many of the protein components in proteoglycans and glycoproteins found in extracellular matrix. Plasmin also has been thought to activate metalloendoproteinases such as the procollagenases which degrade both the interstitial collagens of the stroma and type IV and V collagens of the basement membrane. There is extensive evidence that metalloendoproteinases are important to the metastatic process. In addition to its plasminogen activating activity, urokinase may also act directly to degrade some of the extracellular matrix proteins.

Evidence of the importance of the urokinase in metastasis has come from observations of increase in synthesis and/or secretion of urokinase with transformation in culture, (Dieno, K. et al) Plasminigen Activators to Sugar Degradation in Cancer. Adv. Cancer Res., 44:139–266 (1985); as well as from comparisons of the urokinase activities of malignant neoplasms to that of normal tissues. Pereyra-Alphonso, S., Haedo, A., and Bal de Kier, J. Correlation of Urokinase Type Plasmin Activator Production and Metastacity of Two Murine Mammary Adeno Carcinomas. Int. J. Cancer, 1988.

The oligonucleotides of the invention which are antisense to urokinase plasminogen activator have demonstrated in vivo and in vitro reduction of metastasis of breast cell cancer. Antisense oligos complementary to mouse urokinase plasminogen activator, at 3 μM concentration were found to be nontoxic and to inhibit tumor invasion through an artificial basement membrane. A decrease in plasminogen activator activity after treatment indicates an antisense mechanism. In vivo work in mice showed an extremely significant reduction in lung metastatic nodules for oligo-treated individuals when cancerous cells were injected into the tail vein.

expected for other cancers in which this enzyme is important.

Figure 2:
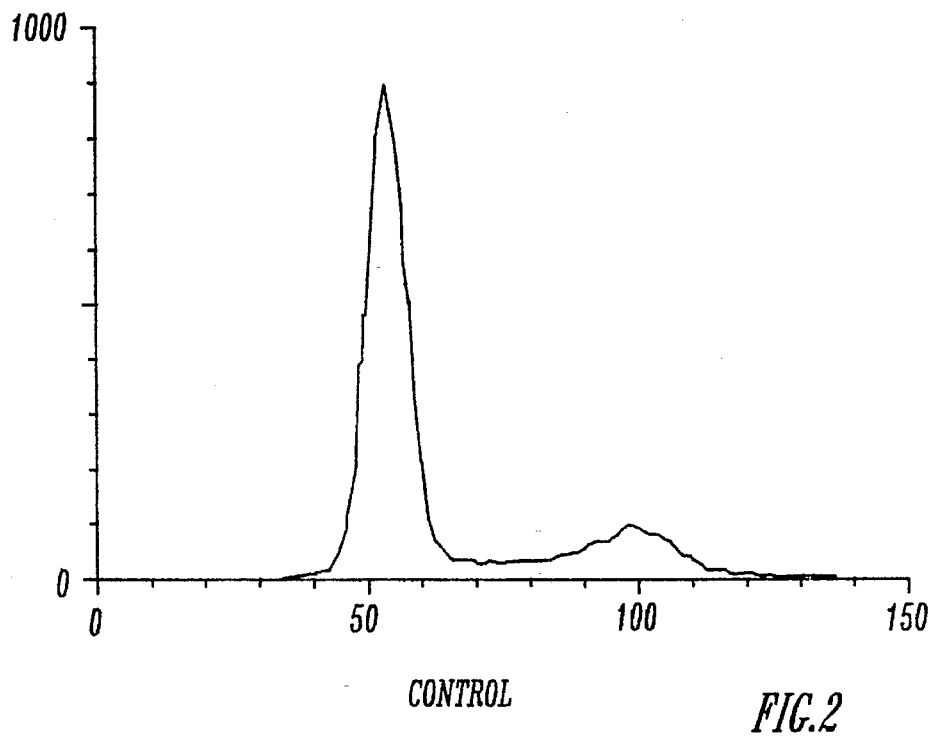
FIGS. 2–4 are depictions of the uninterrupted cell cycle of oligonucleotide treated cells.
Figure 3:
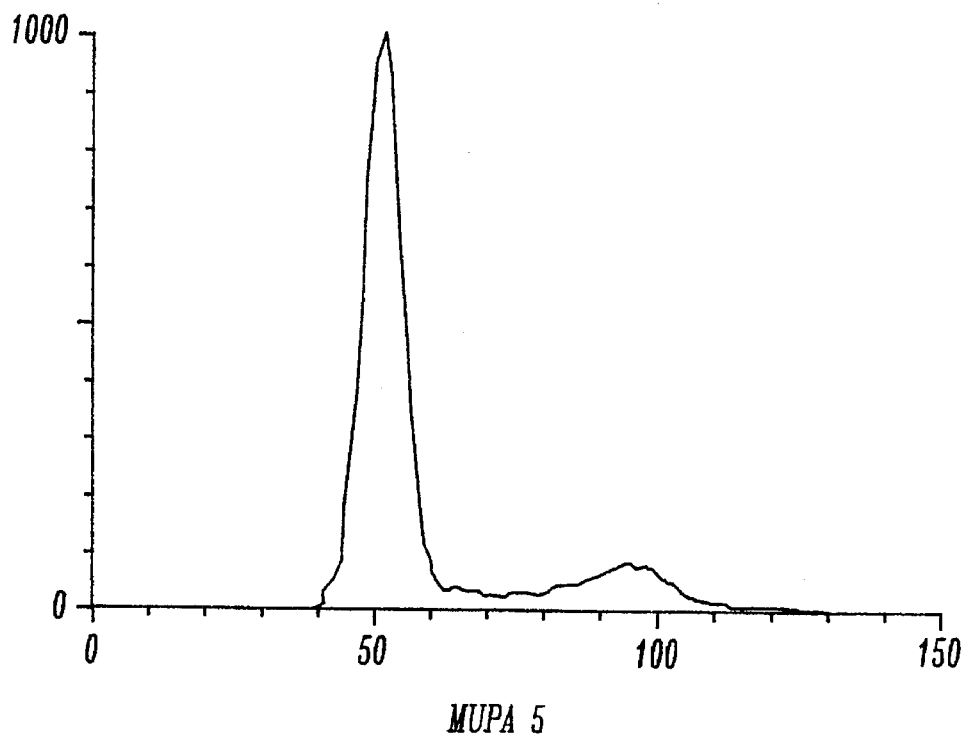
Figure 4:
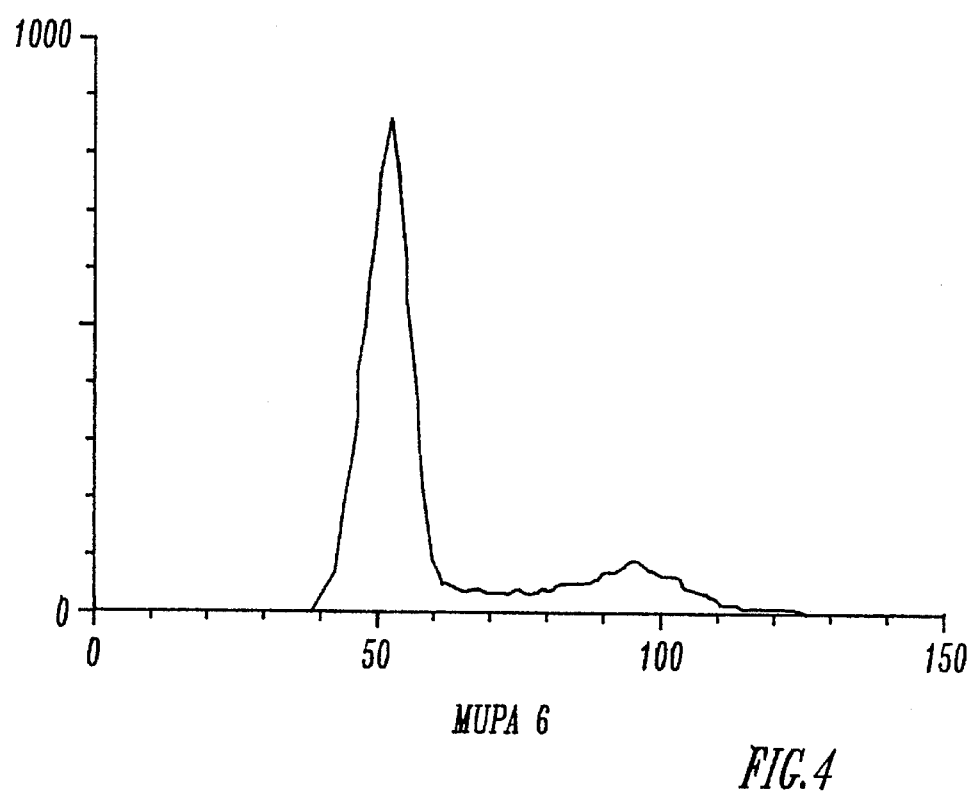

In general, oligonucleotides may work by one or more mechanisms such as hybrid arrest of translation or the oligonucleotide RNA hybrid region can serve as a substrate for RNAse H. The specific actions of the oligonucleotides used here are not known. Cell viability is not affected so invasion is apparently not inhibited due to a cytotoxic effect. In addition, these oligonucleotides produce no alterations in the cell cycle (FIG. 2). Measurement of urokinase type plasminogen activator activity in cells treated with these oligos indicate that these compounds are working through an antisense mechanism. As used herein, the term antisense oligo does not imply any specific mechanism of action within the cell, and merely refers to the design of the oligo.

The following are several examples of inhibition of cell invasion and metastasis of human breast cancer using antisense oligos by the method of the present invention. Although the following describes use of modified oligos which hybridize to select portions of certain proteolytic enzymes, other selected regions as well as other desired target proteases can be selected by those of skill in the art based on the description of the invention.

EXAMPLE 1

In Vitro Activity of Mouse Urokinase Plasminogen Activator Antisense Oligos

In one embodiment of the present invention, antisense oligos designed to the mouse plasminogen activator gene were shown in vitro to reduce the amount of tumor invasion occurring with a highly metastatic line of the BALB-c mammary carcinoma. Antisense oligonucleotides were selected based on the known gene sequence for mouse urokinase plasminogen activator. Target sites for design of antisense oligos are generally known to those of skill in the art, one such site is the ATG initiation site. There are also a variety of computer programs available which may aid in selection and design of oligos.

Oligonucleotide Synthesis and Purification

All chain extension syntheses were performed on an Applied Biosystems Model 380b DNA synthesizer (Foster City, Calif.) using one μM column supports and manufacturer recommended protocols. The identity and homogeneity of the oligonucleotide product was determined by 20% acrylamide and 7% urea polynucleotide gel electrophoresis with visualization by Stains-All (Aldrich). Nucleotide composition and targets for oligonucleotides used are in Table 1.

TABLE 1

| Oligo | Sequence | Target |
| --- | --- | --- |
| MC-7 | 5'-d(GTCCGACGGATAGATGTGAA)-3' (SEQ ID NO: 1) | Cathepsin D |
| MC-8 | 5'-d(CAAGACGCCGGGAGTCTTCAT)-3' (SEQ ID NO: 2) | Cathepsin D |
| MUPA-6 | 5'-d(TTTCGAATTCTCTACTTCAT)-3' (SEQ ID NO: 3) | Urokinase Type Plasminogen Activator |
| MUPA-5 | 5'-d(CTTTGAAGCTCTCTCTCTCT)-3' (SEQ ID NO: 4) | Urokinase Type Plasminogen Activator |
| MUPA-5X | 5'-d(CTTTGAGATCCTCTCTCTCT)-3' (SEQ ID NO: 5) | Urokinase Type Plasminogen Activator (Scramble of 4nt) |
| OL(1)P53 | 5'-d(CCCTGCTCCCCCCTGGCTCC)-3' (SEQ ID NO: 6) | P53 Oncogene |

The tumor model employed was a highly metastatic line of BALB/c mammary carcinoma. Similar results would be

CELL LINES

The BALB/c murine mammary tumor was used for study, and a highly metastatic line was used (410.4) that had been isolated by in vivo selection techniques. (Miller et al, Characterization of Metastatic Heterogeneity Among Subpopulations of a Single Mouse Mammary Tumor: Heterogeneity in Phenotypic Stability Invasion and Metastasis. Invasion Metastasis, 3:22–31, 1983).

TUMOR INVASION ASSAY

Migration of 410.4 cells through matrigel coated Nucleopore filters was measured using Matrigel invasion chambers (Collaborative Biomedical Products). These chambers contained inserts with 8 μM pore size and were coated with a uniform film of matrigel. 4×10⁴ 410.4 cells in Weymouths Medium plus 0.1% bovine serum albumin were added to the invasion chambers. The wells below the invasion chambers contained 0.5 ml of Weymouths plus 10% fetal calf serum as a chemoattractant. The chambers were incubated for 48 hours at 37° to allow the cells to invade through the matrigel into the lower wells. The noninvasive cells were then removed from the upper surface of the membrane with a cotton swab and the cells on the lower surface were stained using a Leucostat staining kit. The membranes then were removed from the chamber using a scalpel and the cells were counted under high power (450×) in 5 random fields. The results can be seen in FIG. 1.

MEASUREMENT OF CELL VIABILITY

Cell viability was determined by the ability of viable cells to take up and reduce 3-(4,5-dimethylthiazol- 2-yl)-2,5-diphenyl tetrazolium bromide (MTT) to a formozan product that can be measured spectrophotometrically at 540 nm. Cole, S. P., Rapid Chemosensitivity Testing of Human Lung Tumor Cells Using the MTT ASSAY. Cancer Chemother. Pharmacol., 17:259–263, 1986. Viability also was determined by propidium iodide staining using the flow cytometer and measuring absorbance at 488 nm.

410.4 cells were treated for 72 hours with the indicated oligonucleotide (3 μM).

TABLE 2

EFFECT OF ANTISENSE OLIGONUCLEOTIDES ON 410.4 CELL VIABILITY

| Oligonucleotide | Viability |
|---|---|
| MC-7(SEQ ID NO: 1) | 125[a] ± 21 |
| MC-8(SEQ ID NO: 2) | 134 ± 25 |
| MUPA(6-SEQ ID NO: 3) | 109 ± 12 |
| MUPA-5(SEQ ID NO: 4) | 97 ± 10 |
| MUPA-5X(SEQ ID NO: 5) | 126 ± 23 |
| OL(1)P53(SEQ. ID NO: 6) | 103 ± -17 |

[a]Percent of untreated control cells ± Standard Deviation.

CELL CYCLE ANALYSIS

Cell cycle analysis was performed by the method of Vindelov using a FACS STAR Plus flow cytometer. Vindelov, L., Christensen, I. J. and Nissen, N. I. Standardization of High-Resolution Flow Cytometric DNA Analysis by the Simultaneous Use of Chicken and Trout Red Blood Cells as Internal Reference Standards. Cytometry, 3:328–331, 1983. Results can be seen in FIG. 2.

ELISA ASSAY

Cell surface urokinase type plasminogen activator was measured after modifications by the method of Pruslin et al. Pruslin, F. H., To, S. E., Winston, R. and Rodman, T. C. Caveats and Suggestions for the ELISA. J. Immunological Meth., 137:27–35, 1991. The assay was carried out on 410.4 cells (1×10⁴) that were treated with the indicated oligo for three days and then plated in Weymouths medium for 24 hours at 37° C. in 96 well immunoassay NUNC plates. The primary antibody was rabbit anti-mouse urokinase IgG obtained from American Diagnostica Inc. (Greenwich, Conn.) and was added diluted 1:200 in 1% BSA. The secondary antibody was affinity purified goat anti-rabbit IgG horseradish peroxidase conjugate (Bio Rad, Richmond, Calif.). Enzyme activity was measured for 1 hour after addition of a 1:1 dilution of ABTS peroxidase substrate and peroxidase solution B (Kirkegaard and Perry, Gaithersburg, Md.). The plates were read kinetically at 405 nm every 30 seconds for 1 hour with an OD max of 0.500.

TABLE 3

ELISA ASSAY FOR UROKINASE TYPE PLASMINOGEN ACTIVATOR

| Oligonucleotide | $V^{max}$ |
|---|---|
| Control | 3.2 ± 0.3[a] |
| MUPA-5(SEQ ID NO: 4) | 2.4 ± –0.9[b] |
| MUPA-6(SEQ ID NO: 3) | 2.7 ± 0.6[b] |
| MUPA-5X(SEQ ID NO: 5) | 4.1 ± 2.9 |

[a]$V^{max}$ in mod/min ± Standard Deviation values are the means from duplicate experiments. Each experiment was done in quadruplicate.
[b]significantly different from control values.

The effect of several phosphorothioate antisense oligonucleotides on 410.4 cell invasion through matrigel coated membranes is seen in FIG. 1. From this figure it can be seen that two oligos had significant effects: MUPA-5(SEQ ID NO:4) and MUPA-6(SEQ ID NO:3). These oligos are complementary to the mRNA of urokinase type plasminogen activator and they significantly decreased invasion of the cell line. In contrast, MC-7(SEQ ID NO:1) and MC- 8(SEQ ID NO:2), two ODNs which were complementary to the mRNA of murine cathepsin D, had no effect. MUPA-5X(SEQ ID NO:5), which was the same base composition but a slightly different order than MUPA-5 also had no effect. Thus the inhibitory effect on invasion was specific to the sequence of the urokinase type plasminogen activator mRNA.

It was important to determine if the effects on tumor invasion were the result of effects on cell growth in general or were specific for the invasive properties of the cell. Table 2 demonstrates that none of the oligos decreased the viability of the 410.4 cells.

FIG. 2 shows that cell cycle parameters were also unaffected by these oligos. Therefore the effects of these compounds on tumor invasion was specific.

To determine if these oligos were acting through an antisense mechanism cell surface urokinase type plasminogen activator was assayed using an elisa assay. Table 4 shows that MUPA-5(SEQ ID NO:4), and MUPA 6(SEQ ID NO:3) significantly decreased enzyme activity while the scrambled oligo nucleotide, MUPA-5X(SEQ ID NO:5) which should not effect tumor invasion, had no significant effect on enzyme activity.

Thus the results of in vitro work of antisense oligos has shown that two antisense oligonucleotides complementary to the mRNA of urokinase type plasminogen activator inhibit 410.4 cell invasion in a range of 30–70% (see FIG. 1). It has been repeatedly demonstrated that there is a good correlation between tumor invasion and metastasis. Yagel, S., Khokha, R., Denhardt, D. T., Kerbel, R. S., Parhar, R. S. and Lala, P. K. Mechanism of Cellular Invasiveness: A Comparison of Amnion Invasion In Vitro and Metastatic Behavior In Vivo. J. Natl. Cancer. Inst., 81:768–775, 1989.

Control cultures failed to inhibit 410.4 cell invasion and involved oligonucleotides with 4 bases out of 20 which were rearranged so that the sequence was 80% identical, and the composition of matter was 100% identical to the active oligos. The lack of effect from several other oligonucleotide sequences suggest the sequence specificity in the In Vitro invasion assay. In addition the MC-7 and MC-8 which were antisense to the mRNA of cathepsin D had no effect on 410.4 cell invasion either. Thus the effect depends on the particular protease being targeted and points out the importance of plasminigen activator in tumor invasion at least in this cell line. Since invasion was not completely inhibited, it is likely that other similar protease enzymes are also important.

EXAMPLE 2

IN VIVO Invasion With Phosphorothioate Oligonucleotides

One oligonucleotide MUPA-5(SEQ ID NO:4) which was able to reduce the metastatic potential by treatment of tumor cells in cell culture was examined for its ability to alter the metastatic properties in an in vivo treatment in mice. Mice were implanted with an ALZET pump delivering 0.1 ml of oligonucleotide per day in a continuous infusion over a period of ten days. The pumps were implanted one day before injecting with $10^5$ 410.4 cells into the tail vein. After four weeks the mice were sacrificed, the lungs removed and fixed with Bouin's solution, and surface tumors counted visually. This experiment was run once with MUPA5 and MUPA5X with counting at 7 days and again with MUPA5, MUPA5X and a control where a phosphate buttered saline solution was administered through the ALZET pump with counting at 14 days. Tables 4A and 4B show the results.

TABLE 4A

| Treatment Group | 7 DAY INFUSION, MEAN ± S.D. |
|---|---|
| MUPA5(SEQ ID NO: 4) (N = 13) | 3.3 ± 2 (0–9) |
| MUPA5X(SEQ ID NO: 5) (N = 13) | 7.6 ± 1.7 (0–21) |

TABLE 4B

| | 14 DAY INFUSION, MEAN ± S.D. |
|---|---|
| Control (N = 13) | 39.9 ± 6 (15–92)[1] |
| MUPA5(SEQ ID NO: 4) (N = 13) | 0.6 ± 0.3 (0–3)[2] |
| MUPA5X(SEQ ID NO: 5) (N = 13) | 8.7 ± 1.9 (0–24)[3] |

[1]Numbers in parenthesis represent the range in the number of metastatic nodules per lung.
[2]Value is extremely significantly different from control, $p < 0.00001$
[3]Value is significantly different from control, $p < 0.05$.

This experiment confirms the ability of antisense oligonucleotides to urokinase plasminogen activator to interfere with the metastatic process when administered in vivo without treating the cells prior to injection. A drastic reduction in lung metastatic nodules was seen 98.5% between the control and the MUPA5 (SEQ ID NO:4) line. This protocol closely mimics the actual sequence of events that would be happening in a person with an operable tumor such as breast cancer.

EXAMPLE 3

In accordance with the present invention human sequences were used to develop antisense oligos for testing. The sequences were selected in the same manner as the mouse sequences.

Synthetic oligonucleotides were prepared as the sodium ion form as apyrogenic, sterile material at Lynx Therapeutics, Inc. in Foster City, Calif.

TABLE 5

| HUMAN SEQUENCE OLIGONUCLEOTIDES UROKINASE PLASMINOGEN ACTIVATOR (HUPA) | | |
|---|---|---|
| Name | Position | Sequence |
| HUPA-ATG start site | 60–79 | 5'GGGCTCTCATGGTGGCGAGG-3'(SEQ ID NO: 7) |
| HUPA-GAIA-9.7 | 1961–1979 | 5'TCCACACAGTTTAAGGAA-3'(SEQ ID NO: 8) |
| HUPA-GAIA-7.5 | 1477–1495 | 5'TGGTGGGTGGCACAGGCAA-3'(SEQ ID NO: 9) |
| HUPA-GAIA-i.7' | 636–654 | 5'AAACCAGGGCTGGTTCTC-3'(SEQ ID NO: 10) |
| HUPA-SCR-CONTROL | N/A | 5'AAACCGAGGCTGGTTCCT-3'(SEQ ID NO: 11) |
| HUPA-303 | 303 | 5'GGCCTTTCCTCGGTAAAA-3'(SEQ ID NO: 12) |
| HUPA1478 | 1478 | 5'TGGTGGTGGCACAGGCAA-3'(SEQ ID NO: 13) |
| HUPA70 | 70 | 5'CAGGGCTCTCATGGTGGC-3'(SEQ ID NO: 14) |
| HUPA1815 | 1815 | 5'AGTGTCTCTGCTCCCCAA-3'(SEQ ID NO: 15) |
| HUPA1728 | 1728 | 5'TATTCATTTCTCAACCAT-3'(SEQ ID NO: 16) |
| HUPA1878 | 1878 | 5'TACACACACATATATATT-3'(SEQ ID NO: 17) |
| HUMAN COLLAGENASE IV | | |
| HCOLIV | | 5'CAGGGGCTGCCAGAGGCTCAT-3'(SEQ ID NO: 18) |

Three of these sequences have been tested using the tumor invasion protocol with matrigel-coated membranes as described in Example 1 and compared to a control with no treatment. The results are shown below in Table 6.

TABLE 6

| OLIGONUCLEOTIDE | % OF CONTROL | % INHIBITION |
|---|---|---|
| HCOLIV | 42 | 58 |
| HUPA70 | 72 | 28 |
| HUPA1815 | 131(stimulated) | — |

As can be seen, compared to the untreated control, infiltration was inhibited by 58% for the collagenase oligo, and 28% for the HUPA 70 oligo.

Other human oligonucleotides to be developed include those complementary to the mRNA of collagenase IV, c-erb-B2 and metalloproteinase inhibitor. These oligonucleotides would be assayed for the ability to inhibit tumor invasion and/or motility in vitro using the matrigel-coated membranes as in Example 1. In addition, the activity of the enzymes could also be assayed for again using the procedures of Example 1. In vivo utility would be tested using nude mice with an Alzet osmotic pump similar to earlier procedures. Based on the utility of the earlier selected antisense oligos for mouse urokinase plasminogen activator, it is expected that the human oligos generated by the same process will likely produce similar effects, reducing tumor cell invasion and metastasis.

Thus applicants have established for the first time that antisense oligonucleotides are a real and viable strategy to pursue to inhibit tumor cell invasion and thus are useful for inhibiting metastasis. This would result for the first time in a cancer treatment that would significantly reduce tumor invasion and metastasis with an agent which is non toxic and efficient.

Thus it can be seen the invention accomplishes at least all of its objectives.

What is claimed is:

1. An oligonucleotide selected from the group consisting of:
   SEQ ID NO:3, 4, 8, 13, 14, 15, 16, 17, and 18.

2. A method for inhibiting basement membrane invasion by a tumor cell in vitro comprising:
   contacting said cell with an oligonucleotide selected from the group consisting of: SEQ ID NO: 3, 4, 8, 13, 14, 15, 16, 17, and 18, whereby basement membrane invasion is inhibited.

3. A method for inhibiting tumor cell invasion and metastasis of tumor cells in a mouse, said tumor cells exhibiting increased synthesis or secretion of urokinase plasminogen activator, comprising:
   administering to said mouse an oligonucleotide selected from the group consisting of SEQ ID NO: 3 and 4, whereby tumor cell invasion and metastasis are inhibited.

4. An oligonucleotide wherein said oligonucleotide is SEQ ID NO:3.

5. An oligonucleotide wherein said oligonucleotide is SEQ ID NO:4.

6. An oligonucleotide wherein said oligonucleotide is SEQ ID NO:8.

7. An oligonucleotide wherein said oligonucleotide is SEQ ID NO:13.

8. An oligonucleotide 33 wherein said oligonucleotide is SEQ ID NO:14.

9. An oligonucleotide wherein said oligonucleotide is SEQ ID NO:15.

10. An oligonucleotide wherein said oligonucleotide is SEQ ID NO:16.

11. An oligonucleotide wherein said oligonucleotide is SEQ ID NO:17.

12. An oligonucleotide wherein said oligonucleotide is SEQ ID NO:18.

13. The method of claim 2 wherein said oligonucleotide is SEQ ID NO:3.

14. The method of claim 2 wherein said oligonucleotide is SEQ ID NO:4.

15. The method of claim 2 wherein said oligonucleotide is SEQ ID NO:8.

16. The method of claim 2 wherein said oligonucleotide is SEQ ID NO:13.

17. The method of claim 2 wherein said oligonucleotide is SEQ ID NO:14.

18. The method of claim 2 wherein said oligonucleotide is SEQ ID NO:15.

19. The method of claim 2 wherein said oligonucleotide is SEQ ID NO:16.

20. The method of claim 2 wherein said oligonucleotide is SEQ ID NO:17.

21. The method of claim 2 wherein said oligonucleotide is SEQ ID NO:18.

22. The method of claim 2 wherein said cancer cells are those of mammary carcinoma.

23. The method of claim 3 wherein said administration of the oligonucleotide results in approximately 3 µM plasma concentrations.

24. The method of claim 3 wherein said administration is by means which place the oligonucleotide into the blood stream of the affected animal.

25. The method of claim 3 wherein said administration occurs in combination with surgery to remove cancerous tumors.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: YES ( x i ) SEQUENCE DESCRIPTION: SEQ ID NO:1:

GTCCGACGGA TAGATGTGAA                                                                                   20

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: YES ( x i ) SEQUENCE DESCRIPTION: SEQ ID NO:2:

CAAGACGCCG GGAGTCTTCA T                                                                    21

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: YES ( x i ) SEQUENCE DESCRIPTION: SEQ ID NO:3:

TTTCGAATTC TCTACTTCAT                                                                            20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: mRNA (i i i) HYPOTHETICAL: NO (i v) ANTI-SENSE: YES (x i) SEQUENCE DESCRIPTION: SEQ ID NO:4:

CTTTGAAGCT CTCTCTCTCT　　　　　　　　　　　　　　　　　　　　　　　　　20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: mRNA (i i i) HYPOTHETICAL: NO (i v) ANTI-SENSE: YES (x i) SEQUENCE DESCRIPTION: SEQ ID NO:5:

CTTTGAGATC CTCTCTCTCT　　　　　　　　　　　　　　　　　　　　　　　　　20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: mRNA (i i i) HYPOTHETICAL: NO (i v) ANTI-SENSE: YES (x i) SEQUENCE DESCRIPTION: SEQ ID NO:6:

CCCTGCTCCC CCCTGGCTCC　　　　　　　　　　　　　　　　　　　　　　　　　20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: mRNA (i i i) HYPOTHETICAL: NO (i v) ANTI-SENSE: YES (x i) SEQUENCE DESCRIPTION: SEQ ID NO:7:

GGGCTCTCAT GGTGGCGAGG　　　　　　　　　　　　　　　　　　　　　　　　　20

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: mRNA (i i i) HYPOTHETICAL: NO (iv) ANTI-SENSE: YES (xi) SEQUENCE DESCRIPTION: SEQ ID NO:8:

TCCACACAGT TTAAGGAA                18

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:9:

TGGTGGGTGG CACAGGCAA                19

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:10:

AAACCAGGGC TGGTTCTC                18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:11:

AAACCGAGGC TGGTTCCT                18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:12:

GGCCTTTCCT CGGTAAAA 18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:13:

TGGTGGTGGC ACAGGCAA 18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:14:

CAGGGCTCTC ATGGTGGC 18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:15:

AGTGTCTCTG CTCCCCAA 18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:16:

TATTCATTTC TCAACCAT 18

(2) INFORMATION FOR SEQ ID NO:17:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:17:

TACACACACA TATATATT                                                              18

(2) INFORMATION FOR SEQ ID NO:18:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:18:

CAGGGGCTGC CAGAGGCTCA T                                                          21